US006924092B1

(12) United States Patent
Marechal et al.

(10) Patent No.: US 6,924,092 B1
(45) Date of Patent: Aug. 2, 2005

(54) SCREENING METHOD INVOLVING MGDG SYNTHASE

(75) Inventors: Eric Marechal, Grenoble (FR); Maryse Block, Claix (FR); Jacques Joyard, Meylan (FR); Roland Douce, Grenoble (FR)

(73) Assignees: Commissariat a L'Energie Atomique, Paris (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/926,169

(22) PCT Filed: Mar. 17, 2000

(86) PCT No.: PCT/FR00/00658

§ 371 (c)(1),
(2), (4) Date: Mar. 15, 2002

(87) PCT Pub. No.: WO00/56919

PCT Pub. Date: Sep. 28, 2000

(30) Foreign Application Priority Data

Mar. 19, 1999 (FR) .............................. 99 03434

(51) Int. Cl.$^7$ ............................ C12Q 1/00; G01N 33/53
(52) U.S. Cl. ............................... 435/4; 435/7.1
(58) Field of Search ................................ 800/281, 279, 800/278; 435/196, 193, 7.1, 174, 4; 428/402.24; 424/1.21, 143.1, 400, 601, 130.1, 184.1; 514/24, 129, 25; 536/23.1

(56) References Cited

U.S. PATENT DOCUMENTS 4,025,331 A * 5/1977 Leber ......................... 504/202
5,702,897 A * 12/1997 Reed et al. ..................... 435/6
5,985,848 A * 11/1999 Furneaux et al. ............. 514/44

FOREIGN PATENT DOCUMENTS

WO          00/56919        9/2000

OTHER PUBLICATIONS

Marechal et al (Plant Lipid Metabolism pp 144–151, 1995).*
E. Marechal, et al., "The Catalytic Site of Monogalactosyldiacylglycerol Synthase from Spinach Chloroplast Envelope Membranes", The Journal of Biological Chemistry, vol. 270, No. 11, 1995, pp. 5714–5722.
E. Marechal, et al., "Kinetic Properties of Monogalactosyldiacylglycerol Synthase from Spinach Chloroplast Envelope Membranes", The Journal of Biological Chemistry, vol. 269, No. 8, 1994, pp. 5788–5798.
G.I. McFadden, et al., "Plastid in Human Parasites", Nature, vol. 381, 1996, p. 482.
M. Shimojima, et al. "Cloning of the Gene for Monogalactosyldiacylglycerol Synthase and its Evolutionary Origin", Proc. Natl. Aca. Sci. USA, vol. 94, 1997, pp. 333–337.
I.T. Szamosi, et al., "Inhibition of Threonine Dehydratase Is Herbicidal", Plan Physiol., 1994, 106: pp. 1257–1260.
Z. Peng, et al., "Some Phosphonic Acid Analogs as Inhibitors of Pyrophosphate–Dependent Phosphofructokinase. A Novel Target In Toxoplasma Gondii", Biochemical Pharmacology, vol. 49, No. 1, pp. 105–113, 1995.
B.A. Kenny, et al., "The Application of High–Throughput Screening To Novel Lead Discovery", Progress in Drug Research, vol. 51, pp. 245–269, 1998.

* cited by examiner

*Primary Examiner*—Mark Navarro
(74) *Attorney, Agent, or Firm*—Oblon, Spivak, McClelland, Maier & Neustadt, P.C.

(57) ABSTRACT

The invention concerns a method for screening and selecting parasiticides (apicomplex phyllum parasites) and/or herbicides and the uses thereof. Said method consists in incubating a substance to be tested with a MGDG synthase and measuring the specific enzymatic activity, after said incubation. The invention also concerns the use of MGDG synthase or a plant isolated plastid membrane for selecting or screening the products inhibiting the activity of the MGDG synthase, capable of being used as active principles against apicomplex parasites and/or of being used as herbicides.

8 Claims, 7 Drawing Sheets

Figure 1:
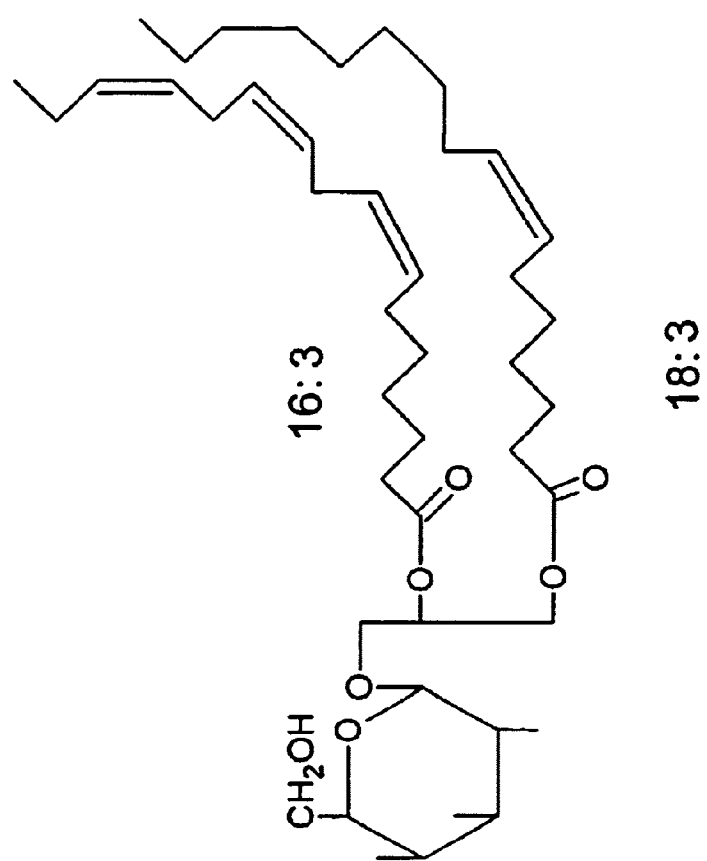

```
soMGD A    MSHPSTVTSEPSN-LLDFVPKLGNFVLNSSLHGNNSNGYSSFSSNSVHFGGLAT----QN  55
csMGD A    MRNPSTVVQENGS-VSDFISQLGYFAFSSRFLNLNSEGCSGSSSHSLYLNGFENYRCVKR  59
atMGD A    MQNPSTVTQESAAPVFDFFPRLRGLTSRNRSPCSNSDGYALSSSNALYFNGFRTLPS-RR  59
atMGD B    ------------------------------------------------------------   0 soMGD A    RYKFVNSLSF---SKEGSNLKRILSDFNRVIRLHCDRI-PLGFSSIGLN--SGESNGVSD  109
csMGD A    PPRSGASLSLS--SRGSSSLRRFVNEFNNVIKFHCHKP-PLGFASLGGV--SDETNGIRD  114
atMGD A    MGKTLASLSFNTKSSAGSSLRRFISDFNSFIRFHCDKVVPESPASVGGVGLSSDENGIRE  119
atMGD B    ----MATTVM---ALAEKVLERVYGTSKSAVSVTSGDGEKTHRHTHHHIHRIKSYDDIDE   53
            :     :      :   *:*:  :    : ::                :  |      : ::: :

soMGD A    NGHG-VLEDVRVPVNAVEPESPKRVLILMSDTGGGHRASAEAIKAAFNEEFGDDYQVFVT  168
csMGD A    DGFG-VSQDGALPLNKIEAENPKRVLILMSDTGGGHRASAEAIKAAFNEEFGNNYQVFIT  173
atMGD A    NGTGGVLGEEGLPLNGVEADRPKKVLILMSDTGGGHRASAEAIRAAFNQEFGDEYQVFIT  179
atMGD B    DESS-------LELIQIGAERTKNVLILMSDTGGGHRASAEAIRDAFKIEFGDKYRVIVK  106
            :    :          : : :: :*:*******************. **:  ***.:*:.:::
                                                          h1 soMGD A    DLWSEHTPWPFNQLPRSYNFLVKHGPLWKMMYYGTSPRVIHQSNFAATSVFIAREVARGL  228
csMGD A    DLWTDHTPWPFNQLPRSYNFLVKHGTLWKMTYYVTAPKVIHQSNFAATSTFIAREVAKGL  233
atMGD A    DLWTDHTPWPFNQLPRSYNFLVKHGTLWKMTYYGTSPRIVHQSNFAATSTFIAREIAQGL  239
atMGD B    DVWKEYTGWPLNDMERSYKFMVKHVQLWKVAFHSTSPKWIHSCYLAAIAAYYAKEVEAGL  166
            *:*::*  **:*:: ***:*:***   ***:  ::  *:*:   :*::  :**  :::  *:*:   **
                                              h2* soMGD A    MKYQPDIIISVHPLMQHVPLRILRGRGLLEKIVFTTVVTDLSTCHPTWFHKLVTRCYCPS  288
csMGD A    MKYRPDIIISVHPLMQHVPIRILRSKGLLNKIVFTTVVTDLSTCHPTWFHKLVTRCYCPS  293
atMGD A    MKYQPDIIISVHPLMQHVPLRVLRSKGLLKKIVFTTVITDLSTCHPTWFHKLVTRCYCPS  299
atMGD B    MEYKPEIIISVHPLMQHIPLWVLKWQELQKRVLFVTVITDLNTCHPTWFHPGVNRCYCPS  226
            *:*:*:************:*: :*:  :  *   :::*::*.******    *:****** soMGD A    NEVAKRATKAGLQPSQIKVYGLPVRPSFVRSVRPKNELRKELGMDEHLPAVLLMGGGEGM  348
csMGD A    TEVAKRALTAGLQPSKLKVFGLPVRPSFVKPIRPKIELRKELGMDENLPAVLLMGGGEGM  353
atMGD A    TEVAKRAQKAGLETSQIKVYGLPVRPSFVKPVRPKVELRRELGMDENLPAVLLMGGGEGM  359
atMGD B    QEVAKRALFDGLDESQVRVFGLPVRPSFARAVLVKDDLRKELEMDQDLRAVLLMGGGEGM  286
            .*****  **.:  *:::*:*********:::   *  :**:**  **::*  ***********
                 h3*                                    h4 soMGD A    GPIEATARALGNALYDANLGEPTGQLLVICGRNKKLAGKLSSIDWKIPVQVKGFVTKIEE  408
csMGD A    GPIEATAKALSKALYDENHGEPIGQVLVICGHNKKLAGRLRSIDWKVPVQVKGFVTKMEE  413
atMGD A    GPIEATARALADALYDKNLGEAVGQVLIICGRNKKLQSKLSSLDWKIPVQVKGFITKMEE  419
atMGD B    GPVKETAKALEEFLYDKENRKPIGQMVVICGRNKKLASALEAIDWKIPVKVRGFETQMEK  346
            **:: **:**  :  ***  :   ::  **::.***** : * ::.***:**:*:*  *:.*:
                 h5* soMGD A    CMGACDCIITKAGPGTIAEAMIRGLPIILNDYIAGQEAGNVPYVIENGIGKYLKSPKEIA  468
csMGD A    CMGACDCIITKAGPGTIAEAMIRGLPIILNDYIAGQEAGNVPYVVENGCGKFSKSPKEIA  473
atMGD A    CMGACDCIITKAGPGTIAEAMIRGLPIILNGYIAGQEAGNVPYVVENGCGKFSKSPKEIS  479
atMGD B    WMGACDCIITKAGPGTIAESLIRSLPIILNDYIPGQEKGNVPYVVENGAGVFTRSPKETA  406
            .****************:.:**.******.**.*** ********:***  *. ***** :
                                                                  h6* soMGD A    KTVSQWFGPKANELQIMSQNALKHARPDAVFKIVHDLDELVRQKIFVRQYSCAA------  522
csMGD A    NIVAKWFGPKADELLIMSQNALRLARPDAVFKIVHDLHELVKQRSFVPQYSG--------  525
atMGD A    KIVADWFGPASKELEIMSQNALRLAKPEAVFKIVHDMHELVRKKNSLPQLSCTA------  533
atMGD B    RIVGEWFSTKTDELEQTSDNARKLAQPEAVFDIVKDIDELSEQRGPLASVSYNLTSSFASLV  468
            : *::**::  ::**  *:** : *:** : *:***:**:.:**:*:.:**   :   :   *
                                             h7*
```

*FIG. 2A*

SCREENING METHOD INVOLVING MGDG SYNTHASE

The present invention relates to a method for screening and for selecting antiparasitic agents (parasites of the apicomplex phylum) and/or herbicides.

Apicomplexes are single-cell parasites responsible for diseases which are among the most serious for the human species: malaria, the primary deadly disease in the world, and toxoplasmosis, one of the two most common opportunist infections in individuals suffering from AIDS. These infectious diseases are spreading, while no treatment at this time makes it possible to eradicate the parasites which cause them: *Plasmodium* which are found in the hepatic cells and red blood cells of individuals suffering from malaria, and *Toxoplasma* which invades, among other things, the brain of individuals suffering from toxoplasmosis.

Specifically, according to the World Health Organization (WHO), malaria affects more than 500 million human beings and causes 2.5 million deaths per year. Malaria kills half the children under the age of 5 in Africa. 40% of the world population live in regions where malaria is present, and these regions spread each year. Pesticide treatments have caused the mosquitoes which are vectors for the parasites (*anopheles*) to become resistant and the parasite itself (4 species of *Plasmodium*, including *Plasmodium falciparum* for 95% of cases) is becoming increasingly resistant to known treatments (in particular chloroquine derivatives). According to estimates, malaria is the first or second (after diarrhea) deadliest disease in the world. The direct and indirect cost of malaria in Africa has gone from 800 million dollars in 1987 to more than 2 billion dollars in 1998. The resistance to treatments and the spread of the regions where malaria is present make this scourge a major challenge of the 21st century.

According to the National Institute of Health (NIH), toxoplasmosis is the primary brain infection in individuals suffering from AIDS. The parasite (*Toxoplasma gondii*) is common and it may be considered that one person in two has been infected, either by eating incorrectly cooked meat or by coming into contact with domestic cats. Toxoplasmosis is serious only in frail individuals, in particular human fetuses and individuals suffering from AIDS. In the case of AIDS, the patients exhibiting a $CD4^+$ level<$100/mm^3$ develop symptoms of toxoplasmosis, in general by reactivation of a prior infection. The known treatments (sulfadiazine and pyrimethamine the most common, but also clindamycin, azithromycin, clarithromycin, dapsone and atavaquone) must sometimes be prescribed indefinitely since, although they are lethal for the parasite in vitro, these substances do not always eliminate the parasite from the body. Since these treatments are sometimes incompatible with tritherapy, prophylaxis is difficult. In the battle which is still to be fought against AIDS, it is therefore fundamental to investigate novel treatments capable of eradicating *Toxoplasma*.

Other apicomplexes, such as those of the *Eimeria* genus, are responsible for coccidiosis in birds and cattle.

Recently, it has become known that these parasites have plant subcellular structures McFadden et al., *Nature*, 1996, 384, 482; Köhler et al., *Science*, 1997, 275, 1485–1489), termed apicoplasts.

These authors have identified, by in-situ hybridization, the plast which contains a 35 kb DNA in *Toxoplasma gondii*: it is an organelle limited by 4 membranes, which is close in evolution to that of green algae. This plast has very rapidly been presented as a weakness of apicomplex parasites (Fichera et Roos, *Nature*, 1996, 390, 407–409). These authors have in particular shown that some antibiotics, such as fluoroquinolones and macrolides, inhibit prokaryotic DNA gyrases and block the replication of this 35 kb DNA, which appears to be necessary for the survival of the parasite. More recently, Waller et al. (PNAS, 1998, 95, 12352–12357) have shown that this plast contains a protein known to synthesize fatty acids in plant chloroplasts, acyl carrier protein or ACP. The ACP precursor contains a transit sequence of the chloroplast type, which allows the protein (the mature ACP, or a fluorescent label of the GFP type fused with the transit sequence of the ACP precursor) to be integrated into the parasite plast.

ACP is not, unfortunately, specific for the plant kingdom, and is found in particular in bacteria of the intestinal tract. It does not therefore constitute a specific target for a medicinal product which would affect only the apicomplexes living as parasites in the body.

The aim of the inventors has therefore been to provide a target specific for apicomplex parasites, in order to select novel medicinal products which are effective against said apicomplex parasites.

They have now found that MGDG synthase (an enzyme which is essential for the biogenesis of the plast envelope) may be a target of choice for active principles against *Plasmodium* (malaria), *Toxoplasma* (toxoplasmosis) and *Eimeria* (coccidiosis), and for herbicides.

Specifically, MGDG (monogalactosyldiacylglycerol, FIG. 1) is known to be in all the plasts analyzed to date: it is the most abundant lipid of plastidial membranes (>50% of the glycerolipids), is vital to plast biogenesis and cell survival and does not exist in the other membrane systems, in particular in animal cells (Douce, Science, 1974, 183, 852–853); the biosynthesis thereof is catalyzed in the envelope by a UDP-galactose: 1,2-diacylglycerol 3-β-D-galactosyl-transferase (EC 2.4..1.46), also named MGDG synthase, according to the following reaction: 1,2-diacylglycerol+UDP-galactose→UDP+1,2-diacyl-3-O-β-D-galactopyranosyl-sn-glycerol.

A subject of the present invention is the use of an MGDG synthase for selecting or screening products which inhibit the activity of MGDG synthase and which can be used as active principles against apicomplex parasites, and in particular those responsible for malaria, for toxoplasmosis and for coccidiosis.

A subject of the present invention is also the use of a plastidial membrane isolated from a plant, for selecting or screening products which inhibit the activity of MGDG synthase and which can be used as active principles against apicomplex parasites, and in particular those responsible for malaria, for toxoplasmosis and for coccidiosis.

A subject of the present invention is also the use of an MGDG synthase for selecting or screening products which inhibit the activity of MGDG synthase and which can be used as herbicides.

A subject of the present invention is also the use of a plastidial membrane isolated from a plant, for selecting or screening products which inhibit the activity of MGDG synthase and which can be used as herbicides.

A subject of the present invention is also a method for screening and for selecting apicomplex antiparasitic agents and/or herbicides, characterized in that it comprises:
 incubating a substance to be tested with an MGDG synthase and
 measuring the specific enzymatic activity, after said incubation.

Inhibition of the enzymatic activity is defined by a decrease in the activity of at least 50%, as a percentage for control activity (activity of the enzyme treated as the test, but in the absence of inhibitor).

In accordance with the invention, said MGDG synthase preferably has an initial specific activity of between 0.1 and 120 μmol of galactose incorporated/h/mg of protein; some recombinant MGDG synthases may have a specific activity greater than 120 μmol of galactose incorporated/h/mg of protein.

In addition, in accordance with the invention, the MGDG synthase is of plant origin (spinach, cucumber or *Arabidopsis*, in particular) and is selected from the group consisting of the purified or recombinant MGDG synthases A and MGDG synthases B.

In accordance with said method, the MGDG synthase/substance to be tested incubation is carried out in an incubation medium containing a buffer adjusted to a pH of between 6 and 9 (MOPS-NaOH, Tris-HCl, $KH_2PO_4$/$K_2HPO_4$, 10 to 250 mM CAPS), in the presence of detergents (3 to 6 Mm CHAPS, or LDAO) of a reducing agent (1–10 mM DTT, or β-mercaptoethanol), of phosphatidylglycerol (0.1–2 mM) and of a salt (KCl or NaCl, 10–300 mM); preferably, said buffer contains 50 mM of MOPS-NaOH, pH 7.8, 4.5 mM of CHAPS, 1.3 mM of phosphatidylglycerol, 1 mM of DTT, 250 mM of $KH_2PO_4$/$K_2HPO_4$ and 250 mM of KCl.

Also in accordance with the invention, the enzymatic activity of the MGDG synthase is measured after constituting micelles, in accordance with the method described in Maréchel et al. (*J. Biol. Chem.*, 1994, 269, 5788–5798).

In accordance with the invention, said apicomplex parasite is selected from the group consisting of *Plasmodium*, *Toxoplasma* and *Eimeria*.

A subject of the present invention is also the use of an MGDG synthase inhibitor selected in accordance with the method defined above, for producing a medicinal product against parasites.

A subject of the present invention is also the use of an MGDG synthase inhibitor selected in accordance with the method defined above, as a herbicide.

Figure 2B:
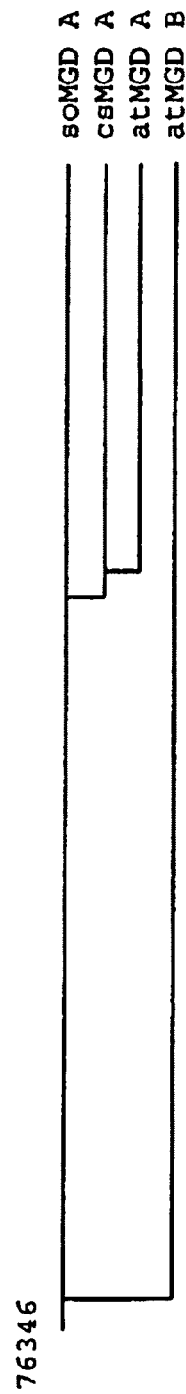
Figure 3A:
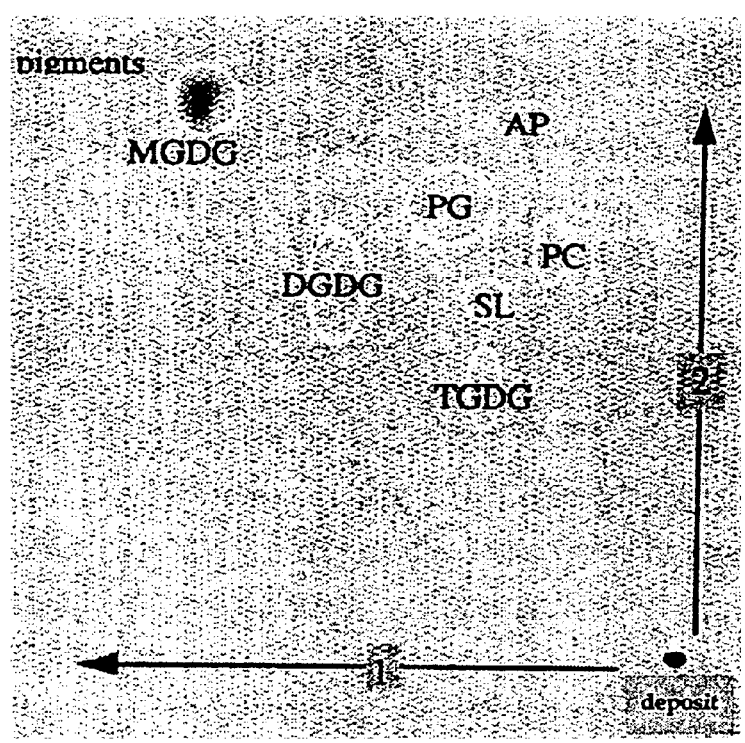
Figure 3B:
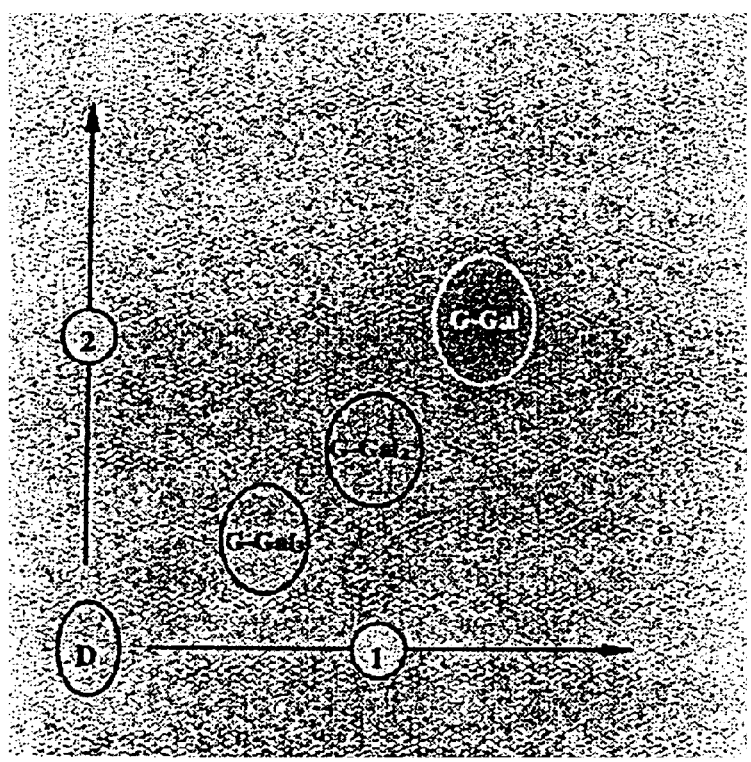
Figure 4:
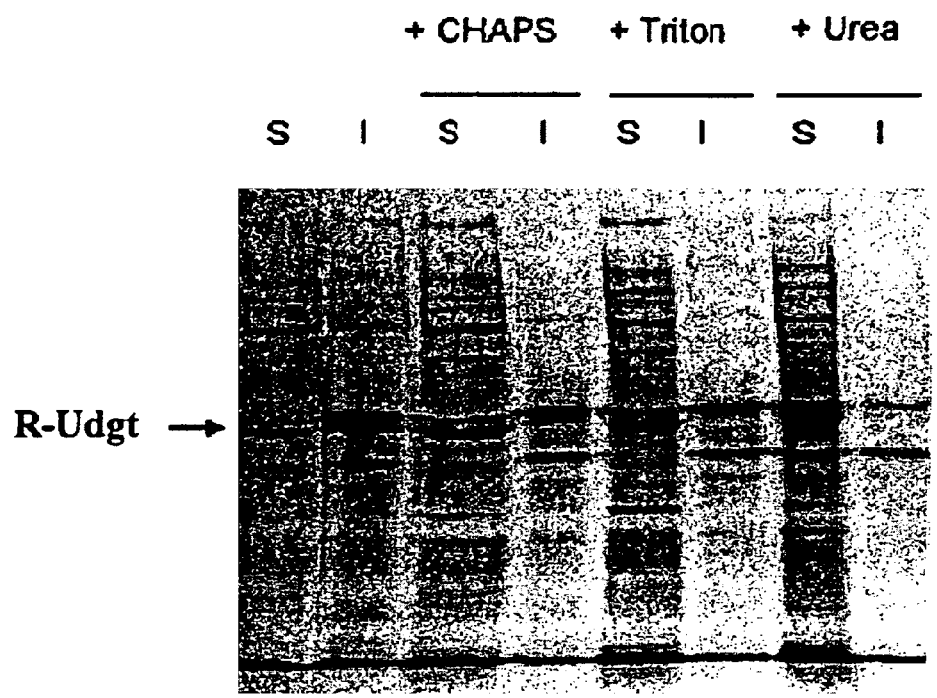
Figures 5A, 5B:
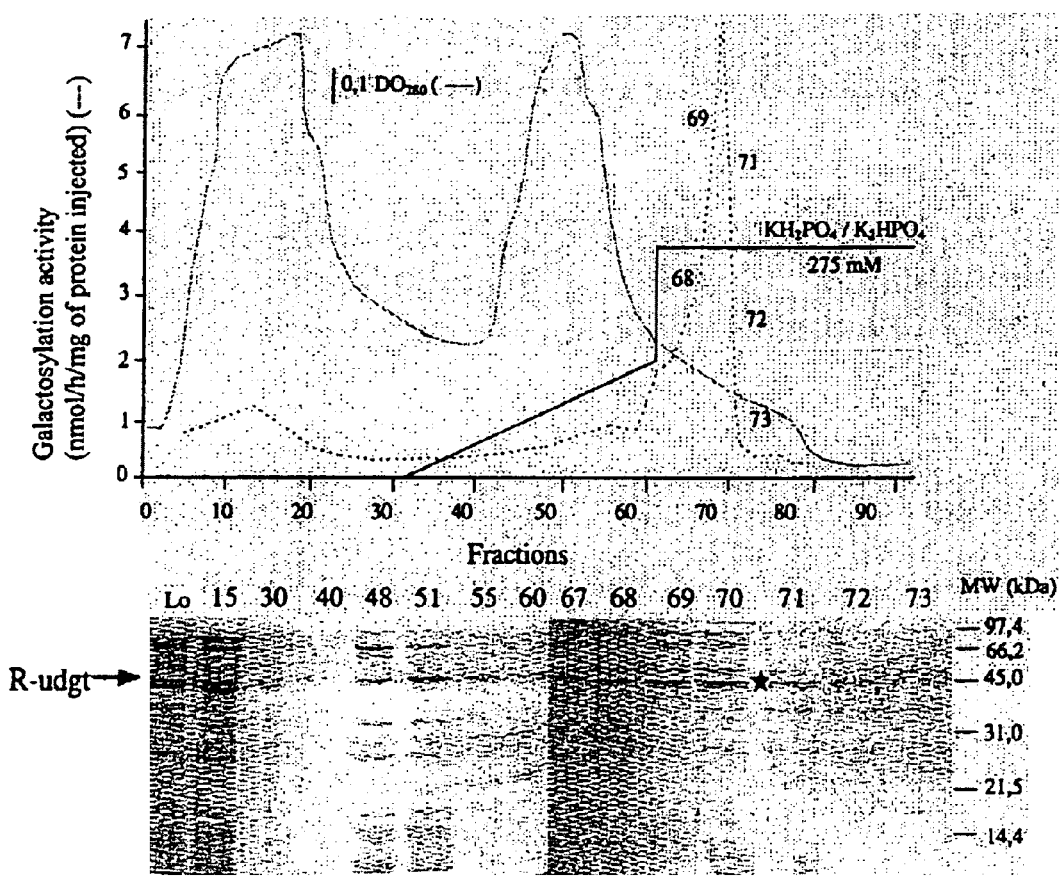

Besides the arrangements above, the invention also comprises other arrangements which will emerge from the following description, which refers to examples of implementation of the method which is the subject of the present invention and also to the attached diagrams, in which:

FIG. 1 represents MGDG (monogalactosyldiacylglycerol);

FIG. 2 is a comparison of spinach, cucumber and *Arabidopsis* MGDG synthase; FIG. 2A corresponds to a comparison of the amino acid sequences deduced from the cDNAs encoding the various MGDG synthases; in this figure, atMGD A (SEQ ID No. 10) and atMGD B (SEQ ID No. 11) correspond to sequences derived from *Arabidopsis thaliana*, csMGD A (SEQ ID No. 9) corresponds to a sequence derived from *Cucumis sativa* and soMGD A (SEQ ID No. 8) corresponds to a sequence derived from *Spinacia oleracea*. * and : represent symbols for the identical amino acids and the conserved substitutions, respectively; h1 to h7 correspond to 7 putative α-helices; FIG. 2B represents a phylogenic tree of mature MGDG synthases;

FIG. 3 corresponds to the identification of the rMGD A reaction product; FIG. 3A: separation of the polar lipids by two-dimensional thin layer chromatography; in this figure, MGDG=monogalactosyldiacylglycerol; DGDG=digalactosyldiacylglycerol; TGDG=trigalacto- syldiacylglycerol; SL=sulfolipid; PC=phosphatidylcholine; PG=phosphatidylglycerol; FIG. 3B corresponds to the analysis of the galactolipids synthesized in vitro by the rMGD A;

FIG. 4 illustrates the location of the rMGD A in *E. coli*;
FIG. 5 corresponds to the partial purification of the rMGD A; FIG. 5A: fractionation by hydroxyapatite agarose chromatography; FIG. 5B: SDS-Page analysis of the fraction eluted from the hydroxyapatite agarose column.

It should be clearly understood, however, that these examples are given by way of illustration of the subject of the invention, of which they in no way constitute a limitation.

EXAMPLE 1

Preparation of an MGDG synthase, from a Plant

The MGDG synthase is solubilized and purified from the envelope of spinach chloroplasts, under the conditions set out in Maréchal et al. (C.R. Acad. Sci. Paris, 1991, 313, III, 521–528; *J. Biol. Chem.*, 1994, 269, 8, 5788–5798; *J. Biol. Chem.*, 1995, 270, 11, 5714–5722).

Specifically:
  the envelope membranes of spinach chloroplasts are purified (see Maréchal et al., *J. Biol. Chem.*, 1995, mentioned above).

The envelope membranes may also be obtained in accordance with the following technique: more precisely, all procedures are carried out at 0°–5° C. The chloroplasts are obtained from 3–4 kg of spinach leaves (*Spinacia oleracea* L.) and purified by isopycnic centrifugation using Percoll gradients. The purified intact chloroplasts are lyzed in a hypotonic medium and the envelope membranes are purified from the lysate by centrifugation in a sucrose gradient.

The envelope membranes obtained are stored under liquid nitrogen, in the medium comprising 50 mM of MOPS-NaOH, pH 7.8 and 1 mM of DTT (dithiothreitol);
  the MGDG synthase is solubilized and purified from the envelope membranes obtained, as specified above (see Maréchal et al., *J. Biol. Chem.* 1995, mentioned above).

The MGDG synthase can also be obtained from cucumber (application JP 10014579 in the name of Kirin Brewery Co. Ltd).

In the context of the implementation of the method according to the present invention, it is preferable to use an MGDG synthase having at least a specific activity of 0.1 μmol of galactose incorporated/h/mg of protein.

EXAMPLE 2

Preparation of a Recombinant MGDG Synthase and Constructs for the Overexpression Thereof in *E. coli*.

1) Cloning and Overexpression of a Class A MGDG [lacuna] in *E. coli*.

Cloning of the MGDG Synthase cDNA:

A 1647 bp fragment corresponding to the mature protein of the cucumber MGDG [lacuna] cDNA (Shimojima et al., 1997) is used as a probe to screen a λgt11 library obtained from spinach leaves.

Before screening, the presence of a homologous mRNA is verified by Northern blot on total RNA from spinach leaves. 320,000 plaques are cultured on *E. coli* Y1090 and transferred onto Hybond-N⁺ membranes. The membranes are prehybridized for 2 h at 60° C. in a solution comprising 2×SSC, 5× Denhardt's, 0.5% SDS (w/v) and salmon sperm DNA (0.1 mg/ml⁻¹).

The hybridization is carried out for 16 h at 60° C. in the same reagent in the presence of 1 ng of [α-$^{32}$P]dCTP-labeled cucumber DNA. The membranes are washed 3 times for 3 min at room temperature in 2×SSC, 0.1% SDS (w/v) and twice for 15 minutes at 55° C., and then autoradiographed.

Two positive clones are then purified by 3 rounds of screening. The phage DNA is extracted and digested with EcoRI or EcoRI and BamHI. The two cDNA inserts are subcloned into the pBlueScript SK+ plasmid (digested with EcoRI or digested with EcoRI-BamHI), for sequencing.

The analysis of the restriction fragment and the sequencing show that the two clones correspond to the same cDNA.

The PCR amplification with primers adjacent to the λgt11 cloning site reveals inserts of 2.5 and 0.9 kb, respectively. The analysis of the sequence of the inserts obtained by PCR shows that the 0.9 kb insert is identical to the 3' end of the 2.5 kb insert.

Consequently, the longest insert is cleaved with the BamHI/EcoRI restriction enzymes, subcloned into the pBlueScript SK+ plasmid (stratagene) and sequenced.

The sequence obtained, which comprises 1851 nucleotides, appears to be a chimera. It contains an 807 nucleotide sequence which is highly homologous to the coding end in 3' of the cucumber MGDG synthase cDNA, including the stop codon. This truncated DNA is fused at its 5' end with a partial DNA sequence (1044 nucleotides) homologous to β-endoglucanases. The 5' end of the MGDG synthase cDNA is cloned by rapid amplification of cDNA ends (RACE) using the Marathon amplification kit (Clontech).

The spinach leaf cDNA is prepared from polyA+ mRNA and used as a matrix for the PCR amplifications of the 5' end of the MGDG synthase cDNA, in accordance with the manufacturer's instructions. The specificity of the reaction comes from the specific primer CTCATTTGAAGGGCAGTAGCACC (nucleotides 870 to 848) (SEQ ID No. 1) and through "hot start" PCR.

This method makes it possible to clone a 1001 bp fragment which is then subcloned into the pBlueScript SK+ plasmid and sequenced on both strands in 3 independent clones, so as to be sure that the Taq polymerase does not introduce any error.

The 5' RACE fragment includes an identifiable initiation codon and 131 nucleotides of the 5' untranslated sequence. The clone comprising the complete MGDG synthase cDNA is generated from the spinach leaf cDNA by PCR, using primers specific for the 3' and 5' ends of the cDNA. The sense primer is as follows: CACACAATATTTCCAATGTATACCCAC (nucleotides −82 to −57) (SEQ ID No. 2).

The antisense primer is as follows: GATTATCATTTCCCCTCGCCCTGCC (nucleotides 1672 to 1648) (SEQ ID No. 3).

The 1765 bp DNA fragment obtained is subcloned into the pBlueScript SK+ plasmid at the SmaI restriction site, and the sequence is verified.

The cDNA sequence is shorter than the transcript (2.5 kb) detected by Northern blot analysis, thus indicating that it is not complete.

The 2 techniques combined (5'-RACE technique and screening of a spinach cDNA library) make it possible to obtain a 1890 bp sequence which includes a 1569 bp open reading frame encoding a 522 amino acid protein (57.5 kDa) (FIG. 2) which belongs to the MGDG synthase A family.

The analysis of the amino acid sequence shows that this MGDG synthase A contains more nonpolar (56%) than polar (44%) residues, 9 cystein residues and 16 histidine residues which may be involved in the chelation of metals; this protein has a basic isoelectric point (pI=9.16).

2) Extraction extraction of the recombinant MGDG synthase (rMGD A) all the procedures are carried out at 4° C. A pellet of recombinant bacteria (34 mg of protein) expressing the MGDG synthase (7 mg of protein) is resuspended in 50 ml of medium A (6 mM of CHAPS, 50 mM of MOPS-NaOH, pH 7.8, 1 mM of DTT) containing 50 mM of $KH_2PO_4$/$K_2HPO_4$ and a mixture of protease inhibitors (1 mM of PMSF; 1 mM of benzamidine; 0.5 mM of caproic acid). After cell lysis by repeated sonication, the suspension is mixed at 0° C. in ice for 30 minutes. The mixture is centrifuged for 15 min at 243 000 g (Beckman L2, SW 40 rotor). The supernatant containing the solubilized proteins (16 mg) is loaded onto a hydroxyapatite ultrogel (IBF-France) column (Pharmacia C10/20, 25 ml of gel), equilibrated with a medium A containing 50 mM of $KH_2PO_4$/$K_2HPO_4$. The proteins are eluted using a gradient of $KH_2PO_4$/$K_2HPO_4$ (50–275 mM) (in a medium A; flow rate: 30 ml/h; fraction volume: 1.5 ml). The recombinant MGDG synthase is eluted at 275 mM of $KH_2PO_4$/$K_2HPO_4$.

3) Overexpression of the Spinach MGDG Synthase in *E. coli*

Materials and Methods

Two mature forms of MGDG synthase are overexpressed in *E. coli*, using the pET-15b plasmid (Novagen) and a plasmid, termed PET-Y 3a, which makes it possible to overcome the problem which comes from the fact that the deduced sequence of the MGDG synthase contains 22 arginine residues, 17 of which are encoded by AGG or AGA, these being codons which are, in fact, used very little in *E. coli*. Specifically, pET-Y 3a was constructed by inserting, into the pET-3a plasmid (Novagen), the arg U (or DNA Y) gene encoding the transfer RNA for arginine, associated with the rare AGA/AGG condons.

These two plasmids are linearized with BamHI and NdeI. The PCR-amplified fragments are generated from the complete cDNA clone. The pET-15 plasmid is ligated with a fragment encoding the 417 C-terminal residues of the enzyme, which is amplified by PCR using the following primers:

sense primer: GGAG<u>CATATG</u>GGGGTGAGTGATAATG (SEQ ID No. 4) and
antisense primer: GTTCT<u>GGATCC</u>TCAAGCAGCA CAA-GAGT (SEQ ID No. 5)
and digested with the BamHI and NdeI enzymes.

Another fragment digested with the BamHI and NdeI enzymes, encoding the 424 C-terminal residues of the enzyme, is amplified by PCR using the following primers:
sense primer: CTTCA<u>CATATG</u>CTTAATTCCGGGGAGAG (SEQ ID No. 6) and
antisense primer: GTTCT<u>GGATC</u>TCAAGCAGCACCGAGTA (SEQ ID No. 7),
and is subcloned into the BamHI-NdeI restriction site of the pET-Y3 plasmid.

The first construct allows the expression of a histidine-tagged fusion protein (hMGD A) comprising 437 residues (48.24 kDA). The second construct allows the expression of a 425 amino acid protein (rMGD A) including an additional initiation methionine corresponding to the ATG codon of the BamHI restriction site. The recombinant proteins are expressed in *E. coli* BI.21(DE3). The bacterial cultures are cultured at 37° C., with vigorous shaking (Certomat, 250 rpm), until an optical density of 0.4 to 0.6 is obtained. Recombinant MGDG synthase expression is induced by adding 0.4 mM of IPTG to the medium and the cultures are incubated for 3 h at 25° C. The bacteria are pelleted by centrifugation (Eppendorf, 14 000 g, 10 min) and solubilized in a buffer A (50 mM MOPS, pH 7.8, 10 mM DTT, 1 mM EDTA, 1 mM benzamidine, 1 mM PMSF and 0.5 mM caproic acid) in the presence or absence of 0.1% Triton X-100 or in a buffer A with 6M urea. The soluble and insoluble fractions are separated by centrifugation (Airfuge, 115 000 g, 15 min) and analyzed on SDS-PAGE (12% polyacrylamide gel). The proteins are detected by staining with Coomassie blue.

The hMGD is purified to homogeneity from the bacteria by affinity chromatography based on a metal (NTA, Novagen), followed by desalification through a PD10 column (Pharmacia) equilibrated in a mixture comprising 5 mM imidazole, 0.5 mM NaCl and 20 mM Tris-HCl, pH7.9, in the presence of 6M urea.

The pure recombinant protein (1 mg) is used to obtain a rabbit polyclonal antibody (Eurogentec, Belgium). The IgG is purified by DEA-trisacryl M (IBF, France) chromatography.

Results

In order to minimize the effect of the N-terminal end of the target chloroplast sequence, the spinach cDNA is expressed from the residue leucine 99, which corresponds to the putative cleavage site of the signal peptide of the cucumber MGD A precursor (Shimojima et al., PNAS, 1997, 94, 333–337).

Using UDP-[$^{14}$C]gal as substrate, it is possible to measure the MGDG synthase activity in the extracts of *E. coli* expressing the rMGD A, after induction with IPTG: more than 2 μmol of galactose are incorporated/h/mg of protein. The activity determined in the extracts of *E. coli* containing the histidine-tagged protein hMGD A is of the same order (1.3 μmol of galactose incorporated/h/mg of protein).

Only an insignificant fraction of [$^4$C]-galactose (less than 0.1 μmol of galactose incorporated/h/mg of protein) is observed in the *E. coli* lipids before induction with IPTG. In addition, no [$^{14}$C]-galactose incorporation is observed in the control bacteria, which express E37, another inner envelope protein (Teyssier et al., Plant J., 1996, 10, 903–912). After 3 h of induction with IPTG, an extract of *E. coli* containing the overexpressed rMGD A is incubated in the presence of UDP-[$^{14}$C]-gal, and the lipids are extracted in order to analyze the reaction products.

The lipid extract is analyzed by two-dimensional thin layer chromatography, at the same time as the envelope lipids added to the mixture as a standard (Douce et al., In *Methods in Plant Biochemistry, Lipids, Membranes and Aspects of Photobiology* (Harwood et al. eds, 1990, 4, 71–103, Academic Press, London). FIG. 3A shows that a single radioactive spot comigrates with the MGDG of origin and is detected by autoradiography. A more extensive characterization of the MGDG was carried out by analyzing the polar groups by two-dimensional paper chromatography; in this case also, a single radioactive spot is detected by autoradiography and comigrates with the glyceryl galactose obtained after deacylation of the envelope MGDG by gentle alkali hydrolysis (FIG. 3B).

These results show that the product formed in *E. coli* is effectively MGDG, which is normally absent in *E. coli* membranes. No other lipid containing galactose is formed, unlike that which is observed after incubating isolated envelope membranes in the presence of UDP-[$^{14}$C]-gal.

MGDG synthase activity is catalyzed by a multigenic family of proteins.

The bireactional mechanism of MGDG synthase activity has been studied using very enriched membrane protein fractions, as has its selectivity for various molecular species of 1,2-diacylglycerol (Maréchal et al., J. Biol. Chem., 1994, 269, 5788–5798). Certain structural properties of the catalytic site have been elucidated: the existence of amino acids which are important for the catalysis (Cys, His, Lys) and the association of the enzyme with divalent metals (Maréchal et al., J. Biol. Chem., 1995, 270, 5714–5722). The functional molecular mass during the inactivation of MGDG synthase has, moreover, been determined by gamma irradiation: the apparent molecular mass of envelope MGDG synthase is 97±5 kDa. Since the mature MGDG synthase polypeptide is close to 45 kDa in size in a denaturing gel, it is probable that, in the envelope, the MGDG synthase is in dimeric form. A functional molecular mass of 114±12 kDa has also been deduced, using the same technique, for purified recombinant MGDG synthase A. This result suggests that MGDG syntheses are probably homodimers.

EXAMPLE 3

Measurement of the Enzymatic Activity, Using Micelles

The activity of the MGDG synthase is measured on various types of sample, depending on the model chosen: plastidial membrane, membrane fractions of *E. coli* overexpressing a recombinant MGDG synthase (rMGD A, 0.7 μg protein/assay, enzyme extracted beforehand from a plant (see Example 1)).

Preparation of Micelles 1.3 mM of phosphatidylglycerol (PG) and 160 μM of diacylglycerol (DAG) are dissolved in chloroform. After evaporating the solvent under argon, 200 μl of incubation medium containing 50 mM of MOPS-NaOH, pH 7.8, 4.5 mM OF CHAPS, 1 mM of DTT, 250 mM of KH$_2$PO$_4$/K$_2$HPO$_4$ and 250 mM of KCl are added and the medium is mixed vigorously so as to resuspend the lipids. 100 μl of fractions containing the MGDG synthase, in the incubation medium, are introduced then the medium is again mixed vigorously and then maintained at 20° C. for 1 h.

This procedure makes it possible to obtain micelles, in accordance with Maréchal et al., 1994, mentioned above.

Enzymatic Reaction

The reaction in the incubation mixture is then initiated by adding 1 mM of UDP-[$^{14}$C]gal (37 Bq/μmol). After 10 min to 1 h, the reaction is stopped by adding a chloroform/methanol mixture (1:2, v/v), the lipids are extracted in accordance with the method of Bligh et al (Can. J. Biochem. Physiol, 1959, 37, 911–917) and the radioactivity of the labeled galactolipids is determined by liquid scintillation counting as described in Covès et al. (FEBS lett., 1986, 208, 401–406). The activity is expressed in μmol of galactose incorporated/h/mg of protein.

A high specific activity, i.e. up to 115–120 mmol of galactose incorporated/h/mg of protein, and even more, can be obtained in a sample rich in MGDG synthase.

3) Specific Activity of the Overexpressed Soluble rMGD A

When the expression of the spinach MGDG synthase in *E. coli* is analyzed, it is observed that most of the protein (rMGD A) is insoluble and that detergents (6 mM of CHAPS or 1% of Triton X-100) only partially solubilize the protein (FIG. 4). On the other hand, almost all the overexpressed protein is solubilized by urea, indicating that most of the MGDG synthase is present in inclusion bodies (FIG. 4). In this fraction, the activity of the MGDG synthase is very low (0.03 μmol of galactose incorporated/h/mg of protein). In fact, the hydroxyapatite chromatography analysis of the *E. coli* fractions solubilized by CHAPS shows that only a small fraction (approximately 0.1%) of the recombinant protein synthesized by the bacterium is active. The experimental conditions used are the same as those used for the envelope MGDG synthase (see above).

In FIG. 4, the rMGD A expression is induced with 0.4 mM of IPTG as specified in Materials and methods above.

Most (50 to 80%) of the activity loaded at the top of the column is found in a narrow peak which is eluted with 275 mM phosphate (FIG. 5A). In this peak, the specific activity of the MGDG synthase is very high: 115 μmol of galactose incorporated/h/mg of protein.

The analysis of the polypeptides present in the various fractions shows that a 45 kDa polypeptide corresponding to the rMGD A is present in the active fractions, but also in the dead volume, in which most of the protein is present in an inactive form (FIG. 5B). This shows that only a fraction (1%) of the protein solubilized by CHAPS is effectively active.

In this FIG. 5B, 20 μl of fraction eluted from the hydroxyapatite column are analyzed by SDS-PAGE (12% polyacrylamide gel); the proteins are detected by staining with Coomassie blue; Lo: sample loaded at the top of the column; 15, 30, etc.: fractions eluted from a column; MW: molecular weight marker (Biorad); the rMGD A is indicated with an arrow and the active rMGD A is found only in fraction 67 to 71.

EXAMPLE 4

Comparison of the Biochemical Properties of the Overexpressed MGD A, with the Chloroplast Envelope MGDG Synthase The analysis of the activity of the MGDG synthase partially purified from spinach leaf chloroplasts (Maréchal et al., J. Biol. Chem., 1995, 270, 5714–5722) demonstrated that DTT can protect the activity of the enzyme against oxidation and that N-ethylmaleimide (NEM) and ortho-phenanthroline are powerful inhibitors of the enzyme.

The overexpressed spinach MGDG synthase has the same properties.

The rMGD A, purified by hydroxyapatite chromatography, is very active in the presence of DTT. If the DTT is removed by chromatography on a Biogel P6-DG column, the MGDG synthase loses 85% of its activity, whereas the addition of DTT maintains its activity.

The fractions of partially purified rMGD A are desalified by chromatography on a Biogel P6-DG (Bio-Rad) column (Pharmacia, C10/40 column, 30 ml of gel) equilibrated in DTT. Aliquots (200 μl) of the fractions are incubated for 40 minutes at 25° C. with gentle stirring, in the presence or absence of DTT. The galactosylation activity is then measured as specified above (see Example 3).

The results obtained are summarized in Table I below:

TABLE I

| Fraction purified on hydroxyapatite | Activity (%) |
| --- | --- |
| Not desalified | 100 |
| Desalified | 15 |
| Desalified + 1 mM DTT | 75 |
| Desalified + 10 mM DTT | 65 |

The activity is expressed as a percentage of the control (not desalified) activity.

Table II shows that the rMGD A is very sensitive to NEM and that protection of the activity is obtained by preincubation in the presence of DAG and/or of PG.

TABLE II

| Pre-incubation (30 min) | Incubation +/− 150 μM NEM (10 min) | Incubation +/− 10 mM DTT (10 min) | Enzymatic reaction | Activity (%) |
| --- | --- | --- | --- | --- |
| DTT | − | − | + PG + DAG + UDP-gal | 100 |
| — | − | + | + PG + DAG + UDP-gal | 101 |
| — | − | − | + PG + DAG + UDP-gal | 37 |
| — | + | + | + PG + DAG + UDP-gal | 35 |
| DTT | + | − | + PG + DAG + UDP-gal | 108 |
| UDP-gal | + | + | + PG + DAG | 32 |
| PG | + | + | + DAG + UDP-gal | 56 |
| PG + DAG | + | + | + UDP − gal | 60 |

In order to obtain the results summarized in Table II, the rMGD A is desalified by chromatography on a Biogel P6-DG (Bio-Rad) column (Pharmacia, C10/40, column, 30 ml of gel) equilibrated in DTT. Aliquots (200 μl) of the fractions are incubated for 30 minutes at 25° C. with gentle stirring, followed by a 10 min incubation in the presence or absence of 150 μM NEM and then a 10 min incubation in the presence or absence of DTT. The galactosilyation activity is then measured as specified above (see Example 3).

The activity is expressed as a percentage of the control activity, i.e. after incubation for 50 min in the presence of 10 mM DTT.

It is also observed that the overexpressed rMGD is inhibited by the hydrophobic chelating agent orthophenanthroline, as shown in Table III below:

TABLE III

| Conditions | Other additions | Activity (%) |
| --- | --- | --- |
| Initial activity (time 0) | — | 100 |
| Without orthophenanthroline | — | 82 |
|  | PG | 87 |
|  | PG + DAG | 78 |
|  | UDP-gal | 72 |
| With orthophenanthroline | — | 43 |
|  | PG | 27 |
|  | PG + DAG | 92 |
|  | UDP-gal | 17 |

The inactivation of the rMGD A by orthophenanthroline is blocked by DAG, but is not affected by UDP-gal.

As emerges from the above, the invention is in no way limited to its methods of implementation, preparation and application which have just been described more explicitly; on the contrary, it encompasses all the variants thereof which may occur to a person skilled in the art, without departing from the context or from the scope of the present invention.

What is claimed is:

1. A method for screening and for selecting antiparasitic agents, herbicides or combinations thereof, comprising incubating a substance to be tested with a monogalactosyldiacylglycerol synthase or with a plastidial membrane isolated from a plant, measuring the specific enzymatic activity, after said incubation; and selecting the substance that is able to inhibit the specific enzymatic activity of the monogalactosyldiacylglycerol synthase.

2. The method as claimed in claim 1, wherein said monogalactosyldiacylglycerol synthase has an initial specific activity of between 0.1 and 120 μmol of galactose incorporated/h/mg of protein.

3. The method as claimed in claim 1, wherein the monogalactosyldiacylglycerol synthase/substance to be tested incubation is carried out in an incubation medium containing a buffer adjusted to a pH of between 6 and 9, in the presence of detergents, a reducing agent, phosphatidylglycerol, a salt or combinations thereof.

4. The method as claimed in claim 3, wherein the incubation medium further comprises 50 mM of MOPS-NaOH, 4.5 mM of CHAPS, 1 mM of DTT, 1.3 mM of phosphatidylglycerol, 250 mM of $KH_2PO_4/K_2HPO_4$ and 250 mM of KCl, and has a pH of 7.8.

5. The method according to claim 1, wherein the monogalactosyldiacylglycerol synthase is of plant origin and is selected from the group consisting of the purified monogalactosyldiacylglycerol synthases A, recombinant monogalactosyldiacylglycerol synthases A, purified monogalactosyldiacylglycerol synthases B, and recombinant monogalactosyldiacylglycerol synthases B.

6. The method as claimed in claim 1, wherein said antiparasitic agent is effective against an apicomplex parasite is selected from the group consisting of *Plasmodium*, *Toxoplasma* and *Eimeria*.

7. The method as claimed in claim 1, wherein the substance is an antiparasitic agent.

8. The method as claimed in claim 1, wherein the substance is a herbicide.

* * * * *

SEQUENCE LISTING

<160> NUMBER OF SEQ ID NOS: 11

<210> SEQ ID NO 1
<211> LENGTH: 23
<212> TYPE: DNA
<213> ORGANISM: Spinacia oleracea

<400> SEQUENCE: 1
ctcatttgaa gggcagtagc acc                                           23

<210> SEQ ID NO 2
<211> LENGTH: 27
<212> TYPE: DNA
<213> ORGANISM: Spinacia oleracea

<400> SEQUENCE: 2
cacacaatat ttccaatgta tacccac                                       27

<210> SEQ ID NO 3
<211> LENGTH: 25
<212> TYPE: DNA
<213> ORGANISM: Spinacia oleracea

<400> SEQUENCE: 3
gattatcatt tcccctcgcc ctgcc                                         25

<210> SEQ ID NO 4
<211> LENGTH: 26
<212> TYPE: DNA
<213> ORGANISM: Spinacia oleracea

<400> SEQUENCE: 4
ggagcatatg ggggtgagtg ataatg                                        26

<210> SEQ ID NO 5
<211> LENGTH: 28
<212> TYPE: DNA
<213> ORGANISM: Spinacia oleracea

<400> SEQUENCE: 5
gttctggatc ctcaagcagc acaagagt                                      28

<210> SEQ ID NO 6
<211> LENGTH: 28
<212> TYPE: DNA
<213> ORGANISM: Spinacia oleracea

<400> SEQUENCE: 6
cttcacatat gcttaattcc ggggagag                                      28

<210> SEQ ID NO 7
<211> LENGTH: 28
<212> TYPE: DNA
<213> ORGANISM: Spinacia oleracea

<400> SEQUENCE: 7
gttctggatc ctcaagcagc accgagta                                      28

<210> SEQ ID NO 8
<211> LENGTH: 522
<212> TYPE: PRT
<213> ORGANISM: Spinacia oleracea

<400> SEQUENCE: 8

```
Met Ser His Pro Ser Thr Val Thr Ser Glu Pro Ser Asn Leu Leu Asp
1               5                   10                  15

Phe Val Pro Lys Leu Gly Asn Phe Val Leu Asn Ser Ser Leu His Gly
            20                  25                  30

Asn Asn Ser Asn Gly Tyr Ser Ser Phe Ser Ser Asn Ser Val His Phe
        35                  40                  45

Gly Gly Leu Ala Thr Gln Asn Arg Tyr Lys Phe Val Asn Ser Leu Ser
    50                  55                  60

Phe Ser Lys Glu Gly Ser Asn Leu Lys Arg Ile Leu Ser Asp Phe Asn
65                  70                  75                  80

Arg Val Ile Arg Leu His Cys Asp Arg Ile Pro Leu Gly Phe Ser Ser
                85                  90                  95

Ile Gly Leu Asn Ser Gly Glu Ser Asn Gly Val Ser Asp Asn Gly His
            100                 105                 110

Gly Val Leu Glu Asp Val Arg Val Pro Val Asn Ala Val Glu Pro Glu
        115                 120                 125

Ser Pro Lys Arg Val Leu Ile Leu Met Ser Asp Thr Gly Gly Gly His
    130                 135                 140

Arg Ala Ser Ala Glu Ala Ile Lys Ala Ala Phe Asn Glu Glu Phe Gly
145                 150                 155                 160

Asp Asp Tyr Gln Val Phe Val Thr Asp Leu Trp Ser Glu His Thr Pro
                165                 170                 175

Trp Pro Phe Asn Gln Leu Pro Arg Ser Tyr Asn Phe Leu Val Lys His
            180                 185                 190

Gly Pro Leu Trp Lys Met Met Tyr Tyr Gly Thr Ser Pro Arg Val Ile
        195                 200                 205

His Gln Ser Asn Phe Ala Ala Thr Ser Val Phe Ile Ala Arg Glu Val
    210                 215                 220

Ala Arg Gly Leu Met Lys Tyr Gln Pro Asp Ile Ile Ser Val His
225                 230                 235                 240

Pro Leu Met Gln His Val Pro Leu Arg Ile Leu Arg Gly Arg Gly Leu
                245                 250                 255

Leu Glu Lys Ile Val Phe Thr Thr Val Thr Asp Leu Ser Thr Cys
            260                 265                 270

His Pro Thr Trp Phe His Lys Leu Val Thr Arg Cys Tyr Cys Pro Ser
        275                 280                 285

Asn Glu Val Ala Lys Arg Ala Thr Lys Ala Gly Leu Gln Pro Ser Gln
    290                 295                 300

Ile Lys Val Tyr Gly Leu Pro Val Arg Pro Ser Phe Val Arg Ser Val
305                 310                 315                 320

Arg Pro Lys Asn Glu Leu Arg Lys Glu Leu Gly Met Asp His Leu
                325                 330                 335

Pro Ala Val Leu Leu Met Gly Gly Gly Glu Gly Met Gly Pro Ile Glu
            340                 345                 350

Ala Thr Ala Arg Ala Leu Gly Asn Ala Leu Tyr Asp Ala Asn Leu Gly
        355                 360                 365

Glu Pro Thr Gly Gln Leu Leu Val Ile Cys Gly Arg Asn Lys Lys Leu
    370                 375                 380

Ala Gly Lys Leu Ser Ser Ile Asp Trp Lys Ile Pro Val Gln Val Lys
385                 390                 395                 400

Gly Phe Val Thr Lys Ile Glu Glu Cys Met Gly Ala Cys Asp Cys Ile
```

-continued

```
                    405                 410                 415
Ile Thr Lys Ala Gly Pro Gly Thr Ile Ala Glu Ala Met Ile Arg Gly
            420                 425                 430
Leu Pro Ile Ile Leu Asn Asp Tyr Ile Ala Gly Gln Glu Ala Gly Asn
            435                 440                 445
Val Pro Tyr Val Ile Glu Asn Gly Ile Gly Lys Tyr Leu Lys Ser Pro
        450                 455                 460
Lys Glu Ile Ala Lys Thr Val Ser Gln Trp Phe Gly Pro Lys Ala Asn
465                 470                 475                 480
Glu Leu Gln Ile Met Ser Gln Asn Ala Leu Lys His Ala Arg Pro Asp
                485                 490                 495
Ala Val Phe Lys Ile Val His Asp Leu Asp Glu Leu Val Arg Gln Lys
            500                 505                 510
Ile Phe Val Arg Gln Tyr Ser Cys Ala Ala
            515                 520

<210> SEQ ID NO 9
<211> LENGTH: 525
<212> TYPE: PRT
<213> ORGANISM: Cucumis sativa

<400> SEQUENCE: 9

Met Arg Asn Pro Ser Thr Val Val Gln Glu Asn Gly Ser Val Ser Asp
1               5                   10                  15
Phe Ile Ser Gln Leu Gly Tyr Phe Ala Phe Ser Ser Arg Phe Leu Asn
                20                  25                  30
Leu Asn Ser Glu Gly Cys Ser Gly Ser Ser Ser His Ser Leu Tyr Leu
            35                  40                  45
Asn Gly Phe Glu Asn Tyr Arg Cys Val Lys Arg Pro Pro Arg Ser Gly
        50                  55                  60
Ala Ser Leu Ser Leu Ser Ser Arg Gly Ser Ser Ser Leu Arg Arg Phe
65                  70                  75                  80
Val Asn Glu Phe Asn Asn Val Ile Lys Phe His Cys His Lys Pro Pro
                85                  90                  95
Leu Gly Phe Ala Ser Leu Gly Gly Val Ser Asp Glu Thr Asn Gly Ile
            100                 105                 110
Arg Asp Asp Gly Phe Gly Val Ser Gln Asp Gly Ala Leu Pro Leu Asn
            115                 120                 125
Lys Ile Glu Ala Glu Asn Pro Lys Arg Val Leu Ile Leu Met Ser Asp
        130                 135                 140
Thr Gly Gly Gly His Arg Ala Ser Ala Glu Ala Ile Lys Ala Ala Phe
145                 150                 155                 160
Asn Glu Glu Phe Gly Asn Asn Tyr Gln Val Phe Ile Thr Asp Leu Trp
                165                 170                 175
Thr Asp His Thr Pro Trp Pro Phe Asn Gln Leu Pro Arg Ser Tyr Asn
                180                 185                 190
Phe Leu Val Lys His Gly Thr Leu Trp Lys Met Thr Tyr Tyr Val Thr
            195                 200                 205
Ala Pro Lys Val Ile His Gln Ser Asn Phe Ala Ala Thr Ser Thr Phe
        210                 215                 220
Ile Ala Arg Glu Val Ala Lys Gly Leu Met Lys Tyr Arg Pro Asp Ile
225                 230                 235                 240
Ile Ile Ser Val His Pro Leu Met Gln His Val Pro Ile Arg Ile Leu
                245                 250                 255
```

```
Arg Ser Lys Gly Leu Leu Asn Lys Ile Val Phe Thr Thr Val Val Thr
            260                 265                 270

Asp Leu Ser Thr Cys His Pro Thr Trp Phe His Lys Leu Val Thr Arg
            275                 280                 285

Cys Tyr Cys Pro Ser Thr Glu Val Ala Lys Arg Ala Leu Thr Ala Gly
    290                 295                 300

Leu Gln Pro Ser Lys Leu Lys Val Phe Gly Leu Pro Val Arg Pro Ser
305                 310                 315                 320

Phe Val Lys Pro Ile Arg Pro Lys Ile Glu Leu Arg Lys Glu Leu Gly
                325                 330                 335

Met Asp Glu Asn Leu Pro Ala Val Leu Leu Met Gly Gly Glu Gly
            340                 345                 350

Met Gly Pro Ile Glu Ala Thr Ala Lys Ala Leu Ser Lys Ala Leu Tyr
            355                 360                 365

Asp Glu Asn His Gly Glu Pro Ile Gly Gln Val Leu Val Ile Cys Gly
    370                 375                 380

His Asn Lys Lys Leu Ala Gly Arg Leu Arg Ser Ile Asp Trp Lys Val
385                 390                 395                 400

Pro Val Gln Val Lys Gly Phe Val Thr Lys Met Glu Glu Cys Met Gly
                405                 410                 415

Ala Cys Asp Cys Ile Ile Thr Lys Ala Gly Pro Gly Thr Ile Ala Glu
            420                 425                 430

Ala Met Ile Arg Gly Leu Pro Ile Ile Leu Asn Asp Tyr Ile Ala Gly
            435                 440                 445

Gln Glu Ala Gly Asn Val Pro Tyr Val Val Glu Asn Gly Cys Gly Lys
    450                 455                 460

Phe Ser Lys Ser Pro Lys Glu Ile Ala Asn Ile Val Ala Lys Trp Phe
465                 470                 475                 480

Gly Pro Lys Ala Asp Glu Leu Leu Ile Met Ser Gln Asn Ala Leu Arg
                485                 490                 495

Leu Ala Arg Pro Asp Ala Val Phe Lys Ile Val His Asp Leu His Glu
            500                 505                 510

Leu Val Lys Gln Arg Ser Phe Val Pro Gln Tyr Ser Gly
            515                 520                 525

<210> SEQ ID NO 10
<211> LENGTH: 533
<212> TYPE: PRT
<213> ORGANISM: Arabidopsis thaliana

<400> SEQUENCE: 10

Met Gln Asn Pro Ser Thr Val Thr Gln Glu Ser Ala Ala Pro Val Phe
1               5                   10                  15

Asp Phe Phe Pro Arg Leu Arg Gly Leu Thr Ser Arg Asn Arg Ser Pro
            20                  25                  30

Cys Ser Asn Ser Asp Gly Tyr Ala Leu Ser Ser Asn Ala Leu Tyr
        35                  40                  45

Phe Asn Gly Phe Arg Thr Leu Pro Ser Arg Arg Met Gly Lys Thr Leu
    50                  55                  60

Ala Ser Leu Ser Phe Asn Thr Lys Ser Ala Gly Ser Ser Leu Arg
65                  70                  75                  80

Arg Phe Ile Ser Asp Phe Asn Ser Phe Ile Arg Phe His Cys Asp Lys
                85                  90                  95

Val Val Pro Glu Ser Phe Ala Ser Val Gly Gly Val Gly Leu Ser Ser
            100                 105                 110
```

```
Asp Glu Asn Gly Ile Arg Glu Asn Gly Thr Gly Val Leu Gly Glu
        115                 120                 125

Glu Gly Leu Pro Leu Asn Gly Val Glu Ala Asp Arg Pro Lys Lys Val
130                 135                 140

Leu Ile Leu Met Ser Asp Thr Gly Gly Gly His Arg Ala Ser Ala Glu
145                 150                 155                 160

Ala Ile Arg Ala Ala Phe Asn Gln Glu Phe Gly Asp Glu Tyr Gln Val
                165                 170                 175

Phe Ile Thr Asp Leu Trp Thr Asp His Thr Pro Trp Pro Phe Asn Gln
            180                 185                 190

Leu Pro Arg Ser Tyr Asn Phe Leu Val Lys His Gly Thr Leu Trp Lys
        195                 200                 205

Met Thr Tyr Tyr Gly Thr Ser Pro Arg Ile Val His Gln Ser Asn Phe
    210                 215                 220

Ala Ala Thr Ser Thr Phe Ile Ala Arg Glu Ile Ala Gln Gly Leu Met
225                 230                 235                 240

Lys Tyr Gln Pro Asp Ile Ile Ser Val His Pro Leu Met Gln His
                245                 250                 255

Val Pro Leu Arg Val Leu Arg Ser Lys Gly Leu Leu Lys Lys Ile Val
                260                 265                 270

Phe Thr Thr Val Ile Thr Asp Leu Ser Thr Cys His Pro Thr Trp Phe
            275                 280                 285

His Lys Leu Val Thr Arg Cys Tyr Cys Pro Ser Thr Glu Val Ala Lys
        290                 295                 300

Arg Ala Gln Lys Ala Gly Leu Glu Thr Ser Gln Ile Lys Val Tyr Gly
305                 310                 315                 320

Leu Pro Val Arg Pro Ser Phe Val Lys Pro Val Arg Pro Lys Val Glu
                325                 330                 335

Leu Arg Arg Glu Leu Gly Met Asp Glu Asn Leu Pro Ala Val Leu Leu
            340                 345                 350

Met Gly Gly Gly Glu Gly Met Gly Pro Ile Glu Ala Thr Ala Arg Ala
        355                 360                 365

Leu Ala Asp Ala Leu Tyr Asp Lys Asn Leu Gly Glu Ala Val Gly Gln
    370                 375                 380

Val Leu Ile Ile Cys Gly Arg Asn Lys Lys Leu Gln Ser Lys Leu Ser
385                 390                 395                 400

Ser Leu Asp Trp Lys Ile Pro Val Gln Val Lys Gly Phe Ile Thr Lys
                405                 410                 415

Met Glu Glu Cys Met Gly Ala Cys Asp Cys Ile Ile Thr Lys Ala Gly
            420                 425                 430

Pro Gly Thr Ile Ala Glu Ala Met Ile Arg Gly Leu Pro Ile Ile Leu
        435                 440                 445

Asn Gly Tyr Ile Ala Gly Gln Glu Ala Gly Asn Val Pro Tyr Val Val
    450                 455                 460

Glu Asn Gly Cys Gly Lys Phe Ser Lys Ser Pro Lys Glu Ile Ser Lys
465                 470                 475                 480

Ile Val Ala Asp Trp Phe Gly Pro Ala Ser Lys Glu Leu Glu Ile Met
                485                 490                 495

Ser Gln Asn Ala Leu Arg Leu Ala Lys Pro Glu Ala Val Phe Lys Ile
            500                 505                 510

Val His Asp Met His Glu Leu Val Arg Lys Lys Asn Ser Leu Pro Gln
        515                 520                 525
```

```
Leu Ser Cys Thr Ala
    530
```

<210> SEQ ID NO 11
<211> LENGTH: 468
<212> TYPE: PRT
<213> ORGANISM: Arabidopsis thaliana

<400> SEQUENCE: 11

```
Met Ala Thr Thr Val Met Ala Leu Ala Glu Lys Val Leu Glu Arg Val
1               5                   10                  15

Tyr Gly Thr Ser Lys Ser Ala Val Ser Val Thr Ser Gly Asp Gly Glu
            20                  25                  30

Lys Thr His Arg His Thr His His Ile His Arg Ile Lys Ser Tyr
        35                  40                  45

Asp Asp Ile Asp Glu Asp Ser Ser Leu Glu Leu Ile Gln Ile Gly
    50                  55                  60

Ala Glu Arg Thr Lys Asn Val Leu Ile Leu Met Ser Asp Thr Gly Gly
65                  70                  75                  80

Gly His Arg Ala Ser Ala Glu Ala Ile Arg Asp Ala Phe Lys Ile Glu
                85                  90                  95

Phe Gly Asp Lys Tyr Arg Val Ile Val Lys Asp Val Trp Lys Glu Tyr
            100                 105                 110

Thr Gly Trp Pro Leu Asn Asp Met Glu Arg Ser Tyr Lys Phe Met Val
        115                 120                 125

Lys His Val Gln Leu Trp Lys Val Ala Phe His Ser Thr Ser Pro Lys
    130                 135                 140

Trp Ile His Ser Cys Tyr Leu Ala Ala Ile Ala Ala Tyr Tyr Ala Lys
145                 150                 155                 160

Glu Val Glu Ala Gly Leu Met Glu Tyr Lys Pro Glu Ile Ile Ile Ser
                165                 170                 175

Val His Pro Leu Met Gln His Ile Pro Leu Trp Val Leu Lys Trp Gln
            180                 185                 190

Glu Leu Gln Lys Arg Val Leu Phe Val Thr Val Ile Thr Asp Leu Asn
        195                 200                 205

Thr Cys His Pro Thr Trp Phe His Pro Gly Val Asn Arg Cys Tyr Cys
    210                 215                 220

Pro Ser Gln Glu Val Ala Lys Arg Ala Leu Phe Asp Gly Leu Asp Glu
225                 230                 235                 240

Ser Gln Val Arg Val Phe Gly Leu Pro Val Arg Pro Ser Phe Ala Arg
                245                 250                 255

Ala Val Leu Val Lys Asp Asp Leu Arg Lys Glu Leu Glu Met Asp Gln
            260                 265                 270

Asp Leu Arg Ala Val Leu Leu Met Gly Gly Gly Glu Gly Met Gly Pro
        275                 280                 285

Val Lys Glu Thr Ala Lys Ala Leu Glu Glu Phe Leu Tyr Asp Lys Glu
    290                 295                 300

Asn Arg Lys Pro Ile Gly Gln Met Val Val Ile Cys Gly Arg Asn Lys
305                 310                 315                 320

Lys Leu Ala Ser Ala Leu Glu Ala Ile Asp Trp Lys Ile Pro Val Lys
                325                 330                 335

Val Arg Gly Phe Glu Thr Gln Met Glu Lys Trp Met Gly Ala Cys Asp
            340                 345                 350

Cys Ile Ile Thr Lys Ala Gly Pro Gly Thr Ile Ala Glu Ser Leu Ile
        355                 360                 365
```

```
Arg Ser Leu Pro Ile Ile Leu Asn Asp Tyr Ile Pro Gly Gln Glu Lys
    370             375             380

Gly Asn Val Pro Tyr Val Val Glu Asn Gly Ala Gly Val Phe Thr Arg
385             390             395                     400

Ser Pro Lys Glu Thr Ala Arg Ile Val Gly Glu Trp Phe Ser Thr Lys
            405             410                     415

Thr Asp Glu Leu Glu Gln Thr Ser Asp Asn Ala Arg Lys Leu Ala Gln
            420             425             430

Pro Glu Ala Val Phe Asp Ile Val Lys Asp Ile Asp Glu Leu Ser Glu
        435             440             445

Gln Arg Gly Pro Leu Ala Ser Val Ser Tyr Asn Leu Thr Ser Ser Phe
    450             455             460

Ala Ser Leu Val
465
```